United States Patent [19]

Frenkel et al.

[11] Patent Number: 5,719,304
[45] Date of Patent: Feb. 17, 1998

[54] ORGANIC PEROXIDE STABILIZATION WITH PHOSPHOMOLYBDIC ACID

[75] Inventors: Peter Frenkel, Longview; Charles Abma, Marshall, both of Tex.

[73] Assignee: Witco Corporation, Greenwich, Conn.

[21] Appl. No.: 656,095

[22] Filed: May 31, 1996

[51] Int. Cl.$^6$ .................................................. C07C 69/96
[52] U.S. Cl. ........................... 558/264; 526/228; 526/233
[58] Field of Search ........................... 558/264; 526/228, 526/233

[56] References Cited

U.S. PATENT DOCUMENTS 5,155,192  10/1992  Boelema et al. .................... 526/228

FOREIGN PATENT DOCUMENTS 52072788  6/1977  Japan .

Primary Examiner—Paul J. Killos
Assistant Examiner—Sreeni Padmanabhan
Attorney, Agent, or Firm—Scully, Scott, Murphy & Presser

[57] ABSTRACT

Organic peroxide compositions which contain phosphomolybdic acid to retard the rate of decomposition of the peroxide compound are disclosed.

16 Claims, No Drawings

ORGANIC PEROXIDE STABILIZATION WITH PHOSPHOMOLYBDIC ACID

BACKGROUND OF THE INVENTION

The present invention relates to organic peroxide compositions, and more specifically to peroxydicarbonate compositions, in which phosphomolybdic acid has been added to retard the rate of decomposition of the peroxide compound.

Organic peroxides, such as peroxydicarbonates, are useful as free-radical initiators in the polymerization or copolymerization of ethylenically unsaturated monomers.

For example, organic peroxides are used as initiators in the polymerization of vinyl halides, such as vinyl chloride or vinyl bromide; vinylidene halides such as vinylidene chloride; and other compounds containing polymerizable unsaturated units. The products of this well known polymerization process have extensive commercial applications.

The polymerization of vinyl halides or the copolymerization of vinyl halides with vinylidene halides is usually conducted in an aqueous medium, i.e., emulsion, solution or suspension polymerization. In such polymerizations, the monomer or mixture of monomers is dispersed in water in the presence of a surfactant and thereafter the polymerization initiated with an organic peroxide. This is a well known reaction that has been widely reported.

All organic peroxides are by their nature hazardous materials. Their usefulness depends on their ability to decompose into free radicals, shown by the following reaction:

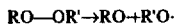

The rate of this decomposition reaction at any given temperature depends on the structure of R and R'.

The decomposition reaction is exothermic. If exothermic decomposition were to occur during production, storage, or shipment, when the peroxides are in a concentrated form, excess pressure development and/or fire or explosion could result. Consequently, many organic peroxides must be kept refrigerated.

There have been several reports in recent years of the retardation of the rate of decomposition of organic peroxides.

The Journal of the American Chemical Society, Volume 72, pages 1254 to 1263 (1950) discloses the use of, for example, ethyl acetoacetate, iodine, trinitrobenzene, acetanilide, nitromethane, phenol, hydrogen peroxide, and tetralin to retard the rate of decomposition of diisopropyl peroxydicarbonate.

U.S. Pat. No. 4,515,929 (1985) reports aqueous dispersions of organic peroxides including peroxydicarbonates, which are stabilized against decomposition by the addition of diphenyl peroxydicarbonate or di(alkyl substituted) phenyl peroxydicarbonates.

U.S. Pat. No 4,552,682 (1985) discloses the use of phenolic antioxidants to retard the rate of degradation of aqueous organic peroxide dispersions. The use of phenolic antioxidants is undesirable because they result in discoloration.

U.S. Pat. No. 5,155,192 (1992) discloses the use of organic hydroperoxides, e.g., tert-butyl hydroperoxide, to retard the rate of decomposition of peroxydicarbonates.

Research Disclosure, April, 1995, page 275, reports the thermal stabilization of dialkyl peroxydicarbonates using unsaturated nitriles or unsaturated acetylenic compounds.

SUMMARY OF THE INVENTION

The present invention relates to the use of certain non-peroxide compounds which are effective in retarding the rate of decomposition of organic peroxides such as peroxydicarbonates. Thus, one aspect of the present invention is a composition containing an organic peroxide compound, such as a peroxydicarbonate, and phosphomolybdic acid which reduces the rate of decomposition of the peroxide compound. Another aspect of the present invention is the method of stabilizing a peroxydicarbonate against decomposition, comprising adding thereto phosphomolybdic acid in an amount effective to achieve said stabilization.

DETAILED DESCRIPTION OF THE INVENTION

The present invention relates to compositions containing an organic peroxide, such as a peroxydicarbonate, and phosphomolybdic acid to retard the rate of decomposition of the peroxide compound.

Phosphomolybdic acid is a term which refers to any of several acidic compounds of phosphorus, molybdenum, oxygen and hydrogen. Without intending to be bound by any particular molecular structure or mode of synthesis, phosphomolybdic acid can be depicted by the formulas $H_3PMo_mO_x$ or $H_3PO_4 \cdot tMoO_3 \cdot dMoO_2$ wherein m (which equals (t+d) is typically 10 to 20 but may be higher than 20 or less than 10, and x is typically 34 to 65 but may be higher than 65 or less than 34, and d may be zero. Preferred phosphomolybdic acid for use in the present invention includes compounds corresponding to the formulas $H_3PMo_{12}O_{40}$ (CAS Registry Nos. 12026-57-2 and 51429-74-4, also known by $P_2O_5 \cdot 20MoO_3 \cdot xH_2O$); $H_3PMo_{12}O_{39}$ (CAS Registry No. 99570-13-5); $H_3PMo_{12}O_{38}$ (CAS Registry No. 99559-64-5); and $H_3PMo_{10}O_{34}$ (CAS Registry No. 12519-76-5). Other phosphomolybdic acids corresponding to these formulas are also contemplated within the present invention. Phosphomolybdic acid is usually associated with up to about 60 moles of water of hydration per mole of phosphomolybdic acid.

The phosphomolybdic acid can be added in solid form but its solubility in inexpensive solvents such as denatured ethanol makes it practical to use solutions of phosphomolybdic acid to add the small amounts desired to the organic peroxide. Other solvents useful in this regard include other alcohols, such as methanol, isopropyl alcohol, n-butanol; ethers, such as diethyl ether; glycols, such as ethylene glycol; esters, such as ethyl acetate; and ketones, such as acetone, methyl ethyl ketone, and diethyl ketone.

The amount of phosphomolybdic acid to use in the compositions of the present invention is an amount sufficient to retard the rate of decomposition of the peroxide compound. The preferred amount of phosphomolybdic acid is a concentration of 0.001 to 1.0% and most preferably 0.02 to 0.1% by weight of the peroxydicarbonate or other organic peroxide present. When the phosphomolybdic acid is added as a solution, the amount of the solution to use is adjusted according to the amount of phosphomolybdic acid present in the solution. The exact amount will vary and depend on the organic peroxide compound, and on the conditions to which the peroxide composition is to be exposed.

Peroxide compounds useful in this invention are of the general structural formula:

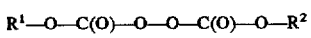

wherein $R^1$ and $R^2$ can each be an aliphatic, cycloaliphatic or aromatic group with 1 to 22 carbon atoms, preferably 2 to 8 carbon atoms. $R^1$ and $R^2$ may be branched or non-branched, substituted or unsubstituted alkyl, alkenyl, cycloalkyl or aromatic groups.

Examples of $R^1$ and $R^2$ groups include phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

Specific examples of peroxydicarbonates include diethyl peroxydicarbonate, di-n-butyl peroxydicarbonate, diisobutyl peroxydicarbonate, and di-4-tert-butylcyclohexyl peroxydicarbonate. Preferably the peroxydicarbonate is di-sec-butyl peroxydicarbonate, di-2-ethylhexyl peroxydicarbonate, di-n-propyl peroxydicarbonate or diisopropyl peroxydicarbonate.

The peroxide compound may be symmetrical or unsymmetrical i.e., $R^1$ and $R^2$ may be the same or different. The peroxide may be a homogeneous mixture containing symmetric peroxides, asymmetric peroxides such as isopropyl-sec-butyl peroxydicarbonate, or a mixture of symmetric and asymmetric peroxides such as mixtures of diisopropyl peroxydicarbonate, di-sec-butyl peroxydicarbonate and isopropyl-sec-butyl peroxydicarbonate as disclosed in U.S. Pat. No. 4,269,726.

The peroxydicarbonate compounds can be synthesized by conventional techniques familiar to one of ordinary skill in the art. Peroxydicarbonates are typically prepared by reacting the corresponding alkyl chloroformate with aqueous sodium peroxide at low temperatures, 0°–20° C. See U.S. Pat. 2,370,588 and the Journal of the American Chemical Society, Volume 72, page 1254 (1950). Other synthetic techniques will be familiar to one of ordinary skill in the art.

Preferably, the peroxydicarbonates useful in this invention include those which are a liquid at 0° C. and more preferably a liquid at −5° C. Still more preferred are the peroxydicarbonates which are liquid down to −20° C.

The present invention is especially applicable to aqueous dispersions of peroxydicarbonates that are useful as initiators in the free radical polymerization of ethylenically unsaturated materials, particularly in an aqueous medium, e.g., suspension or emulsion polymerization. A dispersion of the peroxydicarbonate is prepared by dispersing it in water with a suitable dispersing aid, e.g., a surfactant or emulsifying agent. Surfactants and emulsifying agents useful in the formation of such dispersions are well known in this field and are quite numerous.

To prepare dispersions in accordance with the present invention, the phosphomolybdic acid or a solution thereof may be added to an already-formed peroxide dispersion, or to the water containing the surfactant, or to the peroxide before the dispersion is formed. Dispersions of the present invention generally contain 20 to 70% by weight, preferably 30 to 60% by weight of the peroxydicarbonate or other organic peroxide compound and 0.001 to 1.0% (by weight of the peroxide) of phosphomolybdic acid.

The manner of preparation of peroxide dispersions is known to one of ordinary skill in the art. A description of peroxydicarbonate dispersions and their preparation can be found in U.S. Pat. No. 4,515,929; U.S. Pat. No. 3,825,509; U.S. Pat. No. 3,988,261 and U.S. Pat. No. 4,092,470.

Peroxydicarbonate compositions of the present invention may also be prepared as physical mixtures in the form of liquids, granules, powders or flakes. A physical mixture in accordance with the present invention may be prepared by mixing a liquid peroxide compound, or a solution of a peroxide in a suitable solvent, with the desired amount of phosphomolybdic acid or a solution thereof in a conventional mixing apparatus. The resulting mixture is then, if desired, pulverized or flaked. The phosphomolybdic acid may be added either (1) to the chloroformate-containing reaction mixture before preparation of the peroxide compound or (2) to the unprocessed reaction mixture immediately after preparation of the peroxide compound. Either (1) or (2) will ensure that the two components are mixed as homogeneously as possible in order to receive the greatest possible benefit from the stabilizing effect of the phosphomolybdic acid.

A solution of the present invention may be prepared by combining the desired amounts of phosphomolybdic acid and peroxide in a suitable solvent.

Suitable organic solvents include those normally employed for peroxydicarbonates such as esters of phthalic acid, an example of which is dibutyl phthalate, and aliphatic and aromatic hydrocarbons and mixtures of such hydrocarbons, examples of which are hexane, odorless mineral spirits, mineral oil, benzene, toluene, xylene and (iso) paraffins such as isododecane. Other suitable solvents will be familiar to one of ordinary skill in the art.

Solutions according to the present invention preferably contain at least 10% by weight and more preferably at least 25% by weight of a peroxydicarbonate compound.

The peroxide compositions of the present invention display numerous significant advantages. Chief among these is improved thermal stability, both in response to exposure to elevating temperature and in response to a given constant temperature.

Thermal stability of self-reactive substances, in response to elevating temperatures, can be determined by measuring the self accelerating decomposition temperature or SADT. SADT is one of the recognized tests to determine the safe storage and transportation of materials such as organic peroxides. [Recommendations on the Transport of Dangerous Goods, 9th ed, United Nations, New York 1995, Section 11.3.5, page 264].

SADT can be directly correlated with the onset temperature as measured in a differential thermal analyzer (DTA). The onset temperature is the point at which an uncontrolled thermal decomposition starts. The onset temperature can be measured by determining the point at which the rate of temperature increase in a sealed cell exceeds a certain pre-determined value. In addition, the onset temperature can be measured by determining the point at which the rate of pressure increase in the sealed cell exceeds a certain predetermined value.

Thermal stability in response to a given constant temperature can be assessed by means of accelerated aging tests at, for instance, 15° C.

Phosphomolybdic acid of the present invention increases the onset temperature of peroxydicarbonates. Also, phosphomolybdic acid does not detract from the effectiveness of the peroxide as a polymerization initiator.

The following examples are intended to illustrate the claimed invention and are not in any way designed to limit its scope. Numerous additional embodiments within the scope and spirit of the claimed invention will become apparent to those skilled in the art.

EXAMPLE 1

The onset temperature was measured for samples of pure di-2-ethylhexyl peroxydicarbonate, 2-ethylhexyl peroxydicarbonate diluted in odorless mineral spirits (OMS), and di-sec-butyl peroxydicarbonate diluted in OMS. The onset temperature was also measured for samples of the aforementioned peroxydicarbonates in the presence of various amounts of phosphomolybdic acid. The liquid mixtures were prepared by dissolving the required amount of phosphomolybdic acid solution in the peroxydicarbonate.

Using a type of Differential Thermal Analyzer (Radex Solo Thermal Analyzer, marketed by Astra Scientific International, Pleasanton, Calif.), with an isothermal hold temperature of 30° C. for 15 minutes and then a temperature increase of 1°/minute to 130° C., the onset temperature was measured for a one gram sample of the peroxydicarbonate in a sealed cell. The onset temperature was measured both by noting the point where the rate of increase ($\Delta T$) of the sample temperature reached 0.2° C./minute and also the point where the rate of increase in pressure ($\Delta P$) of the closed sample cell reached 1.0 psi/minute. $\Delta T$ is the difference between the oven temperature and the sample temperature. $\Delta P$ is the difference between a reference pre-calibrated pressure and the pressure developed in the sealed sample cell.

The results, presented in Table I, show that the presence of phosphomolybdic acid increases the temperature at which self accelerating decomposition of the peroxydicarbonate will begin. This shows that the phosphomolybdic acid is an effective stabilizer.

TABLE I

Onset Temperature for Peroxydicarbonates Stabilized with Phosphomolybdic Acid (PMA)

| Peroxide | Wt. % of pure PMA* added | Onset Temperature (°C.) by $\Delta T$ | by $\Delta P$ |
|---|---|---|---|
| 97.7% Di-2-ethylhexyl Peroxydicarbonate (pure) | none | 36.3 | 42.3 |
| 97.7% Di-2-ethylhexyl Peroxydicarbonate (pure) | 0.1 | 50.2 | 53.9 |
| 74.8% Di-2-ethylhexyl Peroxydicarbonate in OMS | none | 41.4 | 43.6 |
| 74.8% Di-2-ethylhexyl Peroxydicarbonate in OMS | 0.62 | 52.6 | 53.5 |
| 74.8% Di-2-ethylhexyl Peroxydicarbonate in OMS | 0.2 | 51.5 | 53.5 |
| 74.8% Di-2-ethylhexyl Peroxydicarbonate in OMS | 0.1 | 53.9 | 54.2 |
| 74.8% Di-2-ethylhexyl Peroxydicarbonate in OMS | 0.04 | 52.5 | 52.0 |
| 74.8% Di-2-ethylhexyl Peroxydicarbonate in OMS | 0.02 | 50.4 | 52.1 |
| 74.8% Di-2-ethylhexyl Peroxydicarbonate in OMS | 0.01 | 47.8 | 47.2 |
| 74.8% Di-2-ethylhexyl Peroxydicarbonate in OMS | 0.004 | 44.3 | 46.5 |
| 76.2% Di-sec-butyl Peroxydicarbonate in OMS | none | 36.6 | 41.0 |
| 76.2% Di-sec-butyl Peroxydicarbonate in OMS | 0.1 | 47.9 | 51.3 |

*added as 20 wt. % solution in denatured ethanol

EXAMPLE 2

The effect of the presence of phosphomolybdic acid on the storage stability at 15° C. of pure di-2-ethylhexyl peroxydicarbonate, di-2-ethylhexyl peroxydicarbonate diluted in odorless mineral spirits (OMS), and di-sec-butyl peroxydicarbonate diluted in OMS, was determined as an accelerated aging test. The purity of the peroxydicarbonate was measured at weekly intervals. The results, presented in Table II, show that phosphomolybdic acid is an effective stabilizer of peroxydicarbonates.

TABLE II

Purity vs. Time for Peroxydicarbonates Stabilized with Phosphomolybdic Acid (PMA)

| Peroxide | Wt. % of pure PMA* Added | % Purity After Storage | | | |
|---|---|---|---|---|---|
| | | 1 week | 2 weeks | 3 weeks | 4 weeks |
| 97.7% Di-2-ethyl-hexyl Peroxy-di-carbonate (pure) | none | 37.3 | 22.4 | 21.6 | 18.8 |
| 97.7% Di-2-ethyl-hexyl Peroxy-di-carbonate (pure) | 0.1 | 94.7 | 84.0 | 76.7 | 69.4 |
| 74.8% Di-2-ethyl-hexyl Peroxy-di-carbonate in OMS | none | 28.6 | 17.9 | 15.4 | 14.9 |
| 74.8% Di-2-ethyl-hexyl Peroxy-di-carbonate | 0.1 | 70.1 | 64.0 | 57.8 | 53.2 |

TABLE II-continued

Purity vs. Time for Peroxydicarbonates
Stabilized with Phosphomolybdic Acid (PMA)

| Peroxide | Wt. % of pure PMA* Added | % Purity After Storage | | | |
|---|---|---|---|---|---|
| | | 1 week | 2 weeks | 3 weeks | 4 weeks |
| 76.2% Di-sec-butyl Peroxydicarbonate in OMS | none | 19.9 | 17.7 | 18.2 | 19.4 |
| 76.2% Di-sec-butyl Peroxydicarbonate in OMS | 0.1 | 60.1 | 46.6 | 39.5 | 37.5 |

*added as 20 wt. % solution in denatured ethanol

We claim:
1. A composition comprising:
   a. an organic peroxide component selected from the group consisting of peroxydicarbonate compounds and mixtures thereof; and
   b. a sufficient amount of phosphomolybdic acid to retard the rate of decomposition of the organic peroxide component.
2. A composition according to claim 1 wherein said organic peroxide component comprises at least one compound of the formula (I)

$$R^1—O—C(O)—O—O—C(O)—O—R^2 \quad (I)$$

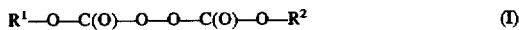

wherein $R^1$ and $R^2$ are independently aliphatic, cycloaliphatic or aromatic groups containing 1 to 22 carbon atoms.
3. A composition according to claim 2 wherein $R^1$ and $R^2$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.
4. A composition according to claim 1 wherein said organic peroxide component is selected from the group consisting of diethyl peroxydicarbonate, isopropyl-sec-butyl peroxydicarbonate, di-n-butyl peroxydicarbonate, di-sec-butyl peroxydicarbonate, di-4-tert-butyl cyclohexyl peroxydicarbonate, di-2-ethylhexyl peroxydicarbonate, di-n-propyl peroxydicarbonate, diisopropyl peroxydicarbonate, and mixtures thereof.
5. A composition according to claim 1 wherein said phosphomolybdic acid comprises 0.001 to 1.0% by weight of said organic peroxide component.
6. A composition according to claim 5 wherein said phosphomolybdic acid comprises 0.02 to 0.1% by weight of said organic peroxide component.
7. A composition according to claim 2 wherein said phosphomolybdic acid comprises 0.001 to 1.0% by weight of said organic peroxide component.
8. A composition according to claim 7 wherein said phosphomolybdic acid comprises 0.02 to 0.1% by weight of said organic peroxide component.
9. The method of retarding the rate of decomposition of an organic peroxide product selected from the group consisting of peroxydicarbonate compounds and mixtures thereof, comprising adding to said organic peroxide product phosphomolybdic acid in an amount thereof effective to retard the rate of said decomposition.
10. A method according to claim 9 wherein said peroxydicarbonate compounds correspond to formula $$R^1—O—C(O)—O—O—C(O)—O—R^2 \quad (I)$$

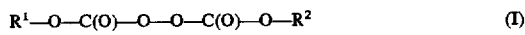

wherein $R^1$ and $R^2$ are independently aliphatic, cycloaliphatic or aromatic groups containing 1 to 22 carbon atoms.
11. A method according to claim 10 wherein $R^1$ and $R^2$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.
12. A method according to claim 9 wherein said organic peroxide component is selected from the group consisting of diethyl peroxydicarbonate, isopropyl-sec-butyl peroxydicarbonate, di-n-butyl peroxydicarbonate, di-sec-butyl peroxydicarbonate, di-4-tert-butyl cyclohexyl peroxydicarbonate, di-2-ethylhexyl peroxydicarbonate, di-n-propyl peroxydicarbonate, diisopropyl peroxydicarbonate, and mixtures thereof.
13. A method according to claim 9 wherein the amount of said phosphomolybdic acid is 0.001 to 1.0% by weight of said organic peroxide product.
14. A method according to claim 13 wherein the amount of said phosphomolybdic acid is 0.02 to 0.1% by weight of said organic peroxide product.
15. A method according to claim 10 wherein the amount of said phosphomolybdic acid is 0.001 to 1.0% by weight of said organic peroxide product.
16. A method according to claim 15 wherein the amount of said phosphomolybdic acid is 0.02 to 0.1% by weight of said organic peroxide product.

* * * * *

UNITED STATES PATENT AND TRADEMARK OFFICE
CERTIFICATE OF CORRECTION

PATENT NO. : 5,719,304

DATED : February 17, 1998

INVENTOR(S) : Peter Frenkel, et al.

It is certified that error appears in the above-identified patent and that said Letters Patent is hereby corrected as shown below:

Column 5, line 13: "AT" should read -- $\Delta$ T--

Signed and Sealed this

Twenty-first Day of March, 2000

Attest:

Attesting Officer

Q. TODD DICKINSON

Commissioner of Patents and Trademarks